United States Patent [19]

Ikari

[11] Patent Number: 5,618,526

[45] Date of Patent: Apr. 8, 1997

[54] COMPOSITION CONTAINING DIVALENT MANGANESE ION

[75] Inventor: Yoshikatsu Ikari, Abiko, Japan

[73] Assignee: Chief Resources Limited, Hong Kong

[21] Appl. No.: 677,580

[22] Filed: Jul. 8, 1996

Related U.S. Application Data

[60] Continuation of Ser. No. 289,564, Aug. 12, 1994, abandoned, which is a division of Ser. No. 49,592, Apr. 20, 1993, Pat. No. 5,368,851, which is a continuation of Ser. No. 827,498, Jan. 30, 1992, abandoned, which is a continuation of Ser. No. 352,253, May 16, 1989, abandoned.

[30] Foreign Application Priority Data

May 16, 1988 [JP] Japan .................................. 63-116958

[51] Int. Cl.⁶ .............................. A61L 9/00; A61K 33/32; A61K 31/34; A61K 31/19
[52] U.S. Cl. ...................... 424/76.1; 424/639; 514/474; 514/574
[58] Field of Search ................................... 424/639, 76.2, 424/76.3, 76.1; 514/474, 574

[56] References Cited

U.S. PATENT DOCUMENTS

| | | | |
|---|---|---|---|
| 3,876,535 | 4/1975 | Young | 210/5 |
| 3,949,098 | 4/1976 | Bangert | 426/324 |
| 4,007,262 | 2/1977 | Bowers | 424/76.1 |
| 4,193,993 | 3/1980 | Hilditch | 424/639 |
| 4,619,829 | 10/1986 | Motschan | 424/639 |
| 4,797,274 | 1/1989 | Miki et al. | 424/76.1 |
| 5,171,726 | 12/1992 | Takemura et al. | 502/170 |
| 5,223,230 | 6/1993 | Takemura et al. | 422/122 |

FOREIGN PATENT DOCUMENTS

| | | |
|---|---|---|
| 1186425 | 4/1985 | Canada . |
| 0147464 | 7/1985 | European Pat. Off. . |
| 60-4127 | 1/1985 | Japan . |
| 642994 | 5/1984 | Switzerland . |

OTHER PUBLICATIONS

Patent Abstracts of Japan, p. 143, C505: JP-A-63 12723 (Shoko Kagaku Kenkyusho K.K.) 1963.

*Primary Examiner*—Raymond Henley, III
*Attorney, Agent, or Firm*—Birch, Stewart, Kolasch & Birch, LLP

[57] ABSTRACT

There is provided a composition containing divalent manganese and a method for preparing the compound. The compound is stable but has good activity and reactivity to be able to use as a deodorizer.

8 Claims, 2 Drawing Sheets

1

COMPOSITION CONTAINING DIVALENT MANGANESE ION

This application is a Rule 62 continuation of application Ser. No. 08/289,564, filed on Aug. 12, 1994, now abandoned, which is a divisional of application Ser. No. 08/049,592, filed on Apr. 20, 1993, now U.S. Pat. No. 5,368,851, which is a Rule 62 continuation of Ser. No. 07/827,498, filed on Jan. 30, 1992, now abandoned, which is a Rule 62 continuation of Ser. No. 07/352,253, filed on May 16, 1989, now abandoned, the entire contents of which are hereby incorporated by reference.

BACKGROUND OF THE INVENTION

1. Field of the Invention

The present invention relates to a composition containing a divalent manganese ion and a method for preparing said composition.

2. Description of the Prior Art

Manganese takes several oxidation forms, such as divalent, trivalent, tetravalent, hexavalent, and heptavalent. In particular, permanganate, in which manganese takes a heptavalent state, exhibits high oxidation power, resulting in it being extensively utilized as an agent for chemical synthesis, analysis, and the like.

Unfortunately, permanganate involves colored property and some safety concerns, due to its high oxidation power. Accordingly, it is disadvantageous in that when it is to be used in the home, it must be carried on a substrate, such as activated carbon.

The most stable of the manganates contain a divalent manganese ion. However, the reactivity of the divalent manganate is low, so that its use range is quite restricted. For example, in a fixing reaction, due to the formation of manganese sulfide by reacting sulfide in the category of an odorous material such as hydrogen sulfide, methyl mercaptan, methyl disulfide, or the like with a divalent manganese compound, the ion-dissociation of the sulfide is increased as its pH changes from neutrality to alkalinity, such that it is necessary to provide the sulfide with a base effect. However, this causes its divalent manganese ion to be insoluble, leading to the formation of manganese hydroxide while exhibiting a chelate effect, which does not contribute to its reactivity.

SUMMARY OF THE INVENTION

The object of the present invention is to provide a novel manganese composition capable of exhibiting improved stability and safety and high reactivity while eliminating the above-described disadvantage of a conventional manganese compound.

The above and other objects, features, and advantages of the invention will become apparent in the following detailed description and drawings.

DETAILED DESCRIPTION OF THE INVENTION

Figure 1:
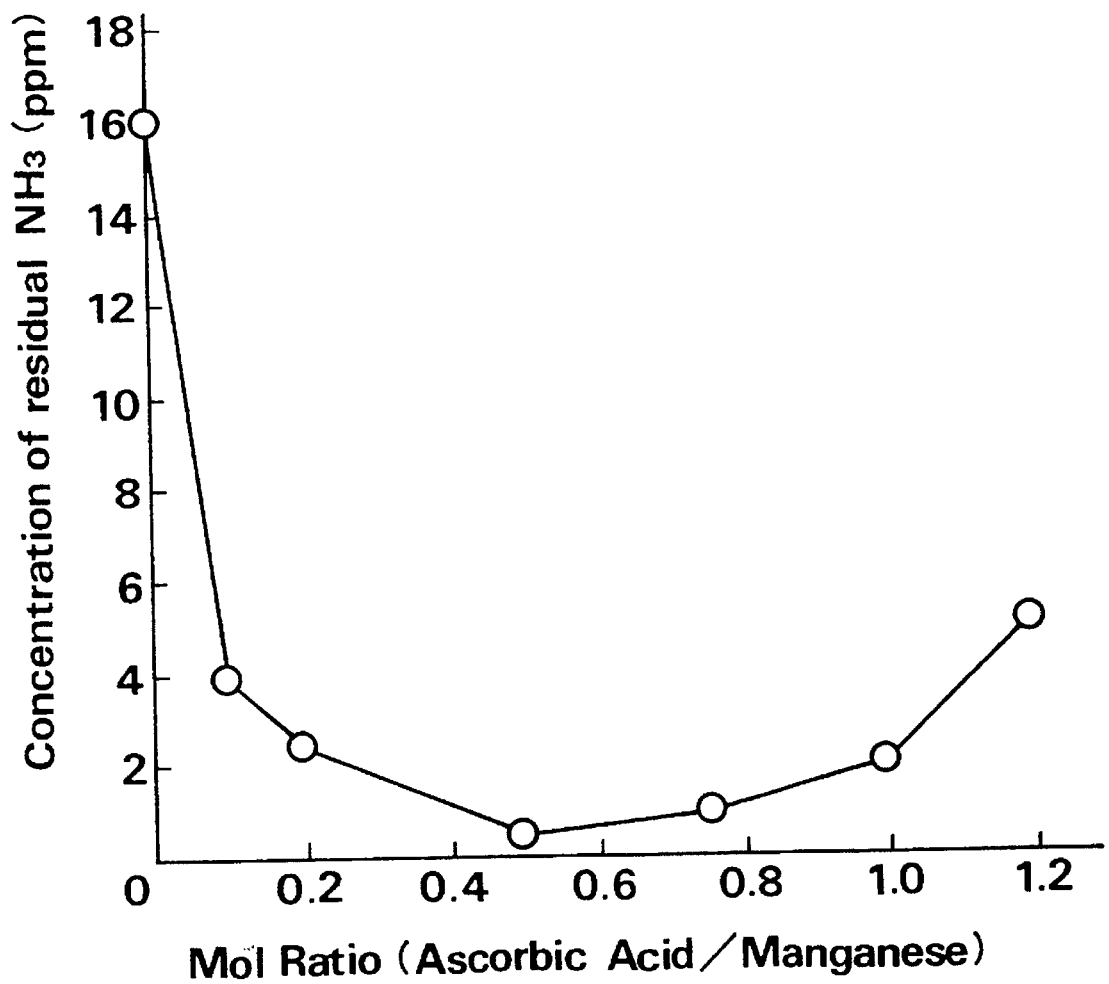
FIG. 1 is a graphic representation showing relationships between a manganese (II)-ascorbic acid composition and its ammonia-adsorption capability.

The inventor, in working to achieve the above-described object, found that the addition of ascorbic acid, which is essential to the human body to a solution containing a water-soluble manganese (II) salt for the purpose of activating a divalent manganese ion, improved the chemical reactivity of manganese (II). It was also found that the addition of ascorbic acid to manganese (II) at an optimum ratio followed by the addition of a material, such as, for example, citric acid or the like, which readily forms a water-soluble complex in cooperation with manganese (II), thereto for the purpose of further improving a chemical reactivity of manganese (II) and maintaining stability of a manganese (II) composition, leads to a composition that exhibits better reactivity and can be effectively used for removing odor. The present invention has been made in view of the above facts.

More particularly, the present invention provides first a manganese (II) composition comprising divalent manganese ion and at least one acid component selected from a group consisting of ascorbic acid, oxypolybasic acids, or their salts.

The present invention also provides for a method of preparing a composition containing manganese (II) comprising mixing at least one acid component selected from a group consisting of ascorbic acid, oxypolybasic acids, or their salts in an aqueous solution of divalent manganese ion.

In the present invention, the ratio of the acid ingredient to the divalent manganese ion is not limited to a specific range, as long as the composition of the present invention mainly consists of the divalent manganese ion. Nevertheless, the molar ratio of the acid ingredient ((L,D-) ascorbic acid or oxypolybasic acid) to the manganese (II) salt or compound is preferably 0.1 to 1.0, more preferably 0.25 to 0.75 (if ascorbic acid is used, it is in an amount 19 to 57 percent by weight based on the manganese (II) compound). Preparation of such a composition may be carried out by adding a suitable amount of the acid ingredient to an aqueous solution of the manganese (II) and dissolving the former in the latter.

When oxypolybasic acid is used as the acid ingredient, a molar ratio of the acid ingredient to the manganese (II) salt is preferably 0.5 to 1.0 (the amount of oxypolybasic acid to the manganese (II) compound being 45 to 91 percent by weight).

The manganese (II) compounds suitable for use in the present invention include both inorganic and organic manganese (II) compounds. Water-soluble manganese (II) salts such as, for example, manganese (II) chloride, manganese (II) nitrate, manganese (II) sulfate, manganese (II) acetate, manganese (II) thiocyanate, and the like may be used for this purpose. A concentration off an aqueous solution of the manganese (II) salt is not limited to a specific range as long as the concentration is included in the range of its solubility. However, it is preferably in the range of 10 to 25% by weight.

Ascorbic acids that may be used as the acid ingredient added to the aqueous manganese (II) solution in the present invention include L-ascorbic acid, which is generally known as vitamin C. D-ascorbic acid is referred to as D-araboascorbic acid or D-erythrobic acid, and it is often used for various purposes because it is readily synthesized, although it exhibits poor physiological activity compared with vitamin C. D-ascorbic acid likewise may be used as the acid ingredient in the present invention. These ascorbic acids each may be used in the form of its alkali metal salt, such as sodium and potassium ascotbate, or its ammonium salt.

Oxypolybasic acids that may be used in the present invention include tartronic acid, malic acid, gluconic acid, citric acid, oxybenzoic acid, salicylic acid, their alkaline metal salts, their ammonium salts, and the like. Of the oxypolyacids, citric acid is conveniently used in view of its utility, such as its low cost and the like. The above-exemplified oxypolybasic acids each form coordinate bonding or chelate bonding with manganese (II), resulting in a composition stable in an aqueous solution.

In the present invention, it is more preferable to coexist the oxypolybasic acid in the manganese (II)-ascorbic acid system.

Such use of the oxypolybasic acid in combination with the ascorbic acid causes a solution of the manganese (II) composition to satisfactorily react with sulfide ions in a gas-liquid contact reaction for contacting the solution with odorous gas in air, even when the pH of the solution is in the acid region, resulting in the removal of a sulfur-containing material. Such function of the solution is promoted correspondingly to neutral fixing of ammonia.

In the present invention, when NaCl or KCl is added in an amount of 3% to 7% by weight to the solution, the ion dissociation is retarded by being accompanied with the increase of ion density, and the oxidation of ascorbic acid due to the dissolved oxygen in the aqueous solution is also retarded to improve the stability of the solution.

Further, the addition of a reducing agent such as $Na_2S_2O_4$, $Na_2SO_3$, and $Na_2S_2O_3$ in an amount of 0.1% to 0.2% by weight to the solution of the present invention is effective to prevent its stability from deterioration which is caused by the presence of an oxidative material. In particular, the reducing agent is excellent in preventing the oxidation of ascorbic acid. The amount of addition below 0.1% is less effective, and when it exceeds 0.2% a negative effect such as generation of gas occurs.

Use of the manganese (II) composition of the present invention is not limited to any specific form. It may be used in the form of its solution. Alternatively, it may take a solid form, which may be obtained by spray-drying or lyophilization. The solid composition may be used in a manner to be mixed with resin or carried on a porous substrate such as paper, activated carbon, or the like by impregnation. The amount of the composition to be carried on the substrate by impregnation may be suitably varied depending on its application. The amount off the composition used in the form of a solution is generally in a range of 10–70% by weight, although it is varied depending on its application.

The mechanism of the reaction by the manganese (II) compound of the present invention has not been made clear. However, it is supposed that, for example, a reaction of the compound with sulfide would be carried out in such a manner that a chelate compound of manganese (II) takes in an oxygen molecule from air and then converts it into active oxygen, so that sulfide caught by the manganese (II) may be oxidized with the active oxygen. A composition free of manganese (II) and consisting of only the acid ingredient, such as ascorbic acid or the like, fails to exhibit such a function because of its weak acidity.

In the composition of the present invention, it is not necessary that the manganese (II) ion component bonds with the acid component from the beginning as long as they bond to each other when the composition is used. Thus the composition of the present invention embraces a sole mixture of the components not bonded to each other.

In order to cause the composition of the present invention to more efficiently carry out the reaction, water preferably coexists. For the same purpose, a small amount of alcohol may be added.

The manganese (II) composition of the present invention exhibits satisfactory stability, activity, and reactivity. Such featured properties of the composition permit it to be used most preferably as a deodorizer capable of removing ammonia, trimethylamine, sulfides, such as hydrogen sulfide, methyl mercaptan and methyl disulfide and the like. It is known that a certain metal complex is substantially colored and deteriorated in stability due to oxidation by oxygen molecules in the air. However, the composition of the present invention is substantially free from discoloration and deterioration in performance, even when it is left standing in the form of a solution for as long as about two months. Also, it does not cause any change in color, even when it is dried. Further, the composition is not substantially colored even after it reacts with a smelly material. Thus, it will be noted that the composition of the present invention exhibits the noteworthy advantage that it is free from coloring even when it is used as an impregnating material or substrate.

The manganese (II) composition of the present invention that exhibits such properties as described above would be extensively used as not only a substrate for removing odors, but as a culture medium for bioindustries, as a functional food agent for human consumption, as a catalyst for oxidation of organic substance, and as a material for an industry in which manganese (II) is used as a raw material. In such applications, the adjustment of the pH of the composition of the present invention from 2 to 6 by the addition of weak alkali causes the advantage of the composition to be more promoted, because the dissociation of sulfide may be readily carried out.

The invention will be described in further detail referring to examples.

EXAMPLE 1

A manganese (II) sulfate solution containing 11.5 g of $MnSO_4 \cdot 4–5H_2O$ in 200 ml of the solution was prepared and L-ascorbic acid was dissolved in the solution in amounts of 0 to 8.80 g, based on 200 ml of the solution, to prepare various solutions containing differing manganese (II) composition.

A water-absorbent paper (20 g) of size 255 mm×80 mm×13 mm and a honeycomb-like structure was impregnated with each of the so-prepared solutions to obtain impregnated papers. Then the impregnated papers were air-dried to cause the composition to be carried on he paper in an amount of 43 to 52 percent by weight based on the weight of the paper and the dry solids content. Each impregnated paper was suspended in a test box having a volume of 0.12 m³, and then gas having an ammonia concentration of about 200 ppm was circulated in the box at a rate of 1.2 m³/min. The concentration of ammonia in the box after ten minutes was measured as an initial concentration, and that after thirty minutes was measured as a residual concentration. The results are shown in FIG. 1.

As is apparent from the results in FIG. 1, it is indicated that the composition consisting of only manganese (II) sulfate failed to exhibit a satisfactory reactivity to ammonia, but the composition in which ascorbic acid coexists was increased in reactivity. More specifically, the addition off ascorbic acid in an amount as small as 0.1 mol caused the ammonia-removing function of the composition to be improved. Such improvement was noteworthy when ascorbic acid was added in an amount of 0.25 to 0.75 mol.

EXAMPLE 2

A manganese (II) sulfate solution containing 11.5 g of $MnSO_4 \cdot 4-5H_2O$ in 200 ml of the solution was prepared as in Example 1. Then, L-ascorbic acid was added to the solution in an amount of 0.5 mol, based on mol of manganese, to prepare a solution (Solution A). To Solution A was added citric acid, which is an oxypolybasic acid, in amounts 0–1.25 mol based on manganese to prepare a series of solutions varying citric acid-concentration (A series). Concurrently, an aqueous solution containing only manganese (II) sulfate (Solution B) was prepared, and then citric acid was added thereto in amounts of 0–1.25 mol, based on manganese to prepare another series (B series) of solutions off varying concentration off citric acid. Then a honeycomb-like water absorbent paper was impregnated with each of the so-prepared solutions and air-dried, to obtain impregnated papers as in Example 1.

Figure 2:
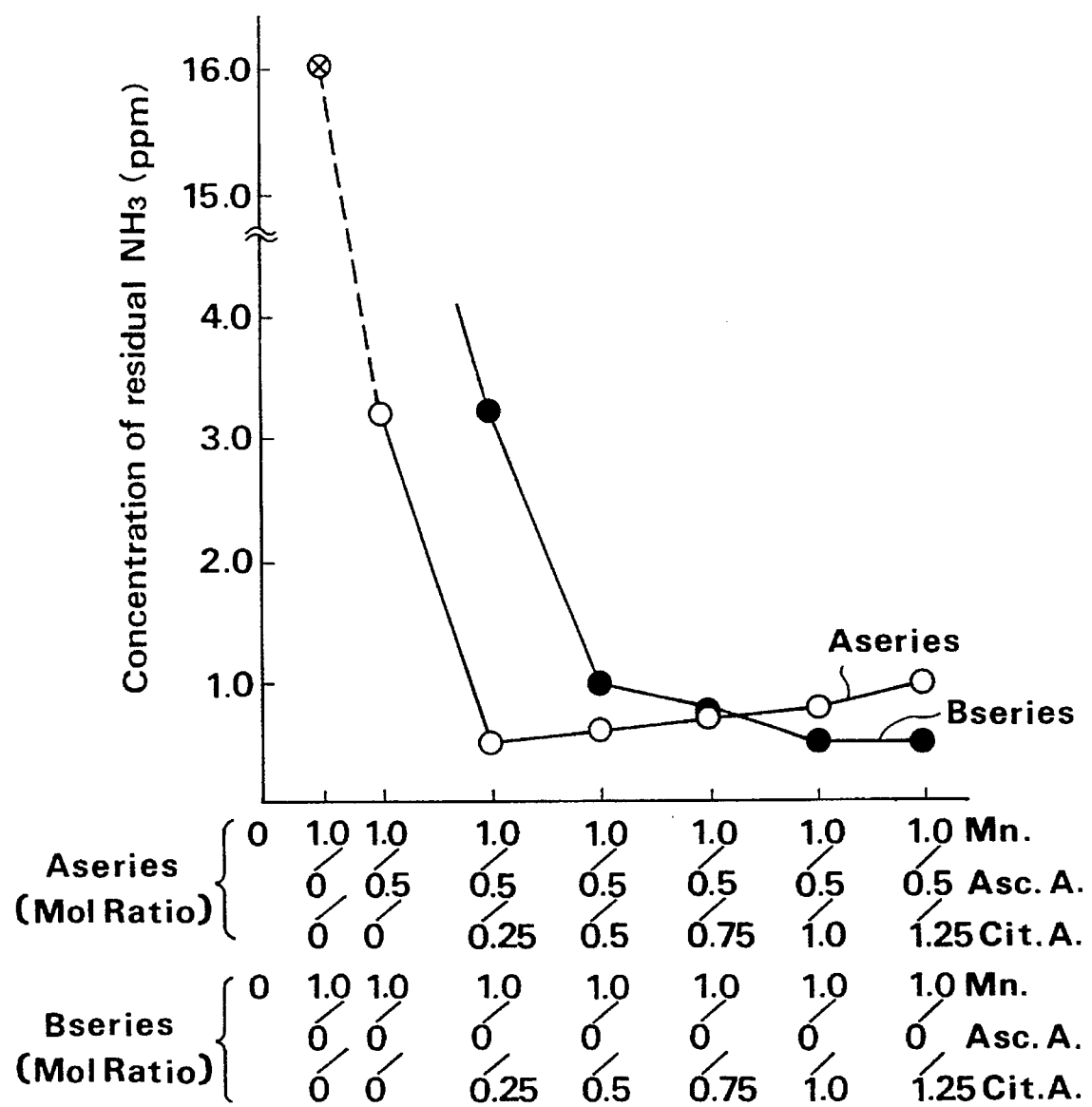
FIG. 2 is a graphic representation showing relationships between a manganese (II)-citric acid composition and its ammonia-adsorption capability.

A deodorizing test was carried out using an apparatus and under conditions similar to Example 1, except that the initial ammonia concentration was set at 400 ppm which is twice that used in Example 1, because it was expected that more amount off ammonia would be adsorbed compared with Example 1. The results are shown in FIG. 2, which clearly indicates that the coexistence off ascorbic acid exhibited satisfactory effects at a region in which the amount off addition off the complex-forming agent to manganese (II) is small, resulting in the ammonia-removing ratio off the composition to be highly improved compared with that obtained due to the ammonia-neutralizing effect off citric acid.

EXAMPLE 3

11.5 g off manganese (II) sulfates tetra- or hepta-hydrate and 4.4 g off ascorbic acid (a molar ratio of 0.5 to manganese) were added to and dissolved in 200 ml of water, and then 5.25 g off citric acid was added thereto to obtain a 20% active manganese (II) aqueous solution. The solution was stored, in place off water, in an ultrasonic humidifier (100 V, 45 W, manufactured by Koshin Co. (Japan)) so that the humidifier was used as atomizer for atomizing the active manganese (II) solution. Then the atomizer was placed in a closed container of size 500 mm×900 mm×480 mm and volume 0.22 m³ equipped with an internal agitating fan, and then hydrogen sulfide gas of a predetermined concentration was fed into the container at a rate of 1.8 m³/min to carry out a contact reaction between the atomized active manganese (II) solution and the hydrogen sulfide gas in the container, during which treated gas was discharged from the container through an outlet, and the concentration of hydrogen sulfide in the gas was measured. The operation was carried out while setting the indicator of the humidifier at a maximum value "9" on the scale, which means that the rate of consumption of the solution was about 40 ml/hr.

The operation was continuously carried out for eight hours, wherein the initial concentration of hydrogen sulfide was set at 1800 ppm, 900 ppm, and 350 ppm, and the concentration of hydrogen sulfide at the outlet is shown an average value.

| Initial Concentration of $H_2S$ (ppm) | Outlet Concentration of $H_2S$ (ppm) | Removal Ratio (%) |
| --- | --- | --- |
| 1800 | 67.5 | 96.1 |
| 900 | 20.1 | 97.7 |
| 350 | 0.0 | 100.0 |

Thus, it will be noted that the composition of the present invention substantially completely treat hydrogen sulfide gas having an initial concentration as high as 500 ppm.

Having described our invention as related to the embodiment, it is our intention that the invention not be limited by any of the details off the description, unless otherwise specified, but rather be construed broadly within its spirit and scope as set out in the accompanying claims.

What we claim is:

1. An oxidation resistant divalent manganese deodorizing composition, comprising:

a divalent manganese ion having an acid component bonded thereto, wherein said acid component comprises (1) citric acid, a salt thereof, or both, and (2) ascorbic acid, a salt thereof, or both; and wherein the molar ratio of said acid component to said divalent manganese ion is in the range of 0.1:1 to 1:1.

2. The composition as claimed in claim 1, wherein the divalent manganese ion comes from a compound selected from the group consisting of manganese (II) chloride, manganese (II) nitrate, manganese (II) sulfate, manganese (II) acetate, and manganese (II) thiocyanate.

3. The composition as claimed in claim 1, wherein the composition is in the form of a solution.

4. The composition as claimed in claim 3, wherein the concentration of said divalent manganese compund in the solution is in the range of 10 to 25% by weight.

5. The composition as claimed in claim 1, wherein the composition is in a solid form.

6. The composition as claimed in claim 5, wherein the composition is carried on a porous substrate.

7. The composition according to claim 3, wherein said solution is an aqueous solution which further comprises a reducing agent in an amount of 0.1% to 0.2% by weight.

8. An oxidation resistant deodorizing composition comprising:

a divalent manganese ion, and an acid component which comprises (1) citric acid, a salt thereof, or both, and (2) ascorbic acid, a salt thereof, or both, and wherein the molar ratio of said acid component to said divalent manganese ion is in the range of 0.1:1 to 1:1.

* * * * *